United States Patent
Kaneda et al.

(10) Patent No.: US 12,239,961 B2
(45) Date of Patent: Mar. 4, 2025

(54) HYDROGENATION REACTION CATALYST USED TO HYDROGENATE AMIDE COMPOUND AND METHOD FOR PRODUCING AMINE COMPOUND USING SAME

(71) Applicants: OSAKA UNIVERSITY, Suita (JP); N.E. CHEMCAT CORPORATION, Minato-ku (JP)

(72) Inventors: Kiyotomi Kaneda, Osaka (JP); Takato Mitsudome, Osaka (JP); Yukio Takagi, Tokyo (JP)

(73) Assignees: OSAKA UNIVERSITY, Suita (JP); N.E. CHEMCAT CORPORATION, Minato-ku (JP)

( * ) Notice: Subject to any disclaimer, the term of this patent is extended or adjusted under 35 U.S.C. 154(b) by 1286 days.

(21) Appl. No.: 16/496,998

(22) PCT Filed: Mar. 28, 2018

(86) PCT No.: PCT/JP2018/012955
§ 371 (c)(1),
(2) Date: Sep. 24, 2019

(87) PCT Pub. No.: WO2018/181563
PCT Pub. Date: Oct. 4, 2018

(65) Prior Publication Data
US 2020/0016576 A1 Jan. 16, 2020

(30) Foreign Application Priority Data
Mar. 31, 2017 (JP) .................................. 2017-070127

(51) Int. Cl.
*B01J 23/648* (2006.01)
*B01J 27/18* (2006.01)
(Continued)

(52) U.S. Cl.
CPC ........... *B01J 23/6482* (2013.01); *B01J 37/04* (2013.01); *C07C 209/50* (2013.01); *B01J 27/1806* (2013.01)

(58) Field of Classification Search
CPC ...... B01J 23/6482; B01J 37/04; C07C 209/50
See application file for complete search history.

(56) References Cited

U.S. PATENT DOCUMENTS

| | | | |
|---|---|---|---|
| 2002/0087036 A1* | 7/2002 | Haas | C07C 209/72 568/885 |
| 2007/0191642 A1* | 8/2007 | Loenders | C07C 211/08 564/488 |
| 2013/0277273 A1* | 10/2013 | Mazyar | C10G 49/00 208/143 |

FOREIGN PATENT DOCUMENTS

| | | | |
|---|---|---|---|
| JP | 10-195030 | 7/1998 | |
| JP | 2012121843 A * | 6/2012 | C07B 43/04 |

(Continued)

OTHER PUBLICATIONS

Machine Translation of JP-2016160243 produced on Jan. 6, 2023 (Year: 2023).*

(Continued)

*Primary Examiner* — Michael Forrest
(74) *Attorney, Agent, or Firm* — Oblon, McClelland, Maier & Neustadt, L.L.P.

(57) ABSTRACT

A catalyst, which can be used even under mild conditions and also has durability so as to enable repeated use while maintaining high activity, and with which a reduction reaction for converting an amide compound into an amine compound can be carried out, is provided by means of an amide compound hydrogenation reaction catalyst characterized in that platinum and vanadium are supported on a carrier and a method for producing an amine compound using the same.

12 Claims, 3 Drawing Sheets

(51) Int. Cl.
*B01J 37/04* (2006.01)
*C07C 209/50* (2006.01)

(56) References Cited

FOREIGN PATENT DOCUMENTS

JP          2016-160243         9/2016
WO     WO 2005/066112 A1    7/2005

OTHER PUBLICATIONS

Mitsudome et al (Mild Hydrogenation of Amides to Amines over a Platinum-Vanadium Bimetallic Catalyst, Angew. Chem. Int. Ed. 2017, 56, 9381-9385). (Year: 2017).*

International Search Report issued on Jun. 19, 2018 in PCT/JP2018/012955 filed on Mar. 28, 2018.

Miyagawa, K. et al., "High selective reduction reaction from amide to amine using molecular hydrogen by Ru-V bimetallic catalyst", Symposium A proceedings of $116^{th}$ Catalyst Symposium, 2015, p. 136.

Burch, R. et al., "Catalytic hydrogenation of tertiary amides at low temperatures and pressures using bimetallic Pt/Re-based catalysts", Journal of Catalysis, vol. 283, 2011, pp. 89-97.

Stein, M. et al., "Catalytic Hydrogenation of Amides to Amines under Mild Conditions", Angewandte Chemie International Edition, vol. 52, 2013, pp. 2231-2234.

Balaraman, E. et al., "Direct Hydrogenation of Amides to Alcohols and Amines under Mild Conditions", JACS Communications, vol. 132, 2010, pp. 16756-16758.

Office Action issued on Jul. 13, 2022, in corresponding Japanese Patent Application No. 2018-062581 (with machine English translation).

* cited by examiner

HYDROGENATION REACTION CATALYST USED TO HYDROGENATE AMIDE COMPOUND AND METHOD FOR PRODUCING AMINE COMPOUND USING SAME

TECHNICAL FIELD

The present invention relates to a catalyst, which is used in a hydrogenation reaction for converting an amide compound into an amine compound, contains platinum and vanadium, and is supported on a carrier, and a method for producing an amine compound using the same.

BACKGROUND ART

A reduction reaction for converting an amide compound into an amine compound is one of the most difficult reactions in reduction of carboxylic acid derivatives because an amide is hardly reducible.

In the reduction reaction for converting an amide compound into an amine compound, a method stoichiometrically using a powerful reducing agent such as lithium aluminum hydride ($LiAlH_4$) or sodium borohydride ($NaBH_4$) is generally used in a small scale test such as a research, however, the reaction has a problem that when such an agent is used for industrial scale synthesis, a large amount of metal waste is generated, or since such an agent has high reactivity, the use thereof in a large amount generates hydrogen or the like and therefore is danger, and an operation such as a post-treatment is complicated, and so on.

On the other hand, a reduction reaction for converting an amide into an amine using molecular hydrogen as a reducing agent produces only harmless water as a by-product, and therefore is an environmentally compatible amine synthesis method. Such an amide catalytic hydrogen reduction reaction has been studied for a long time, and has been carried out using a copper-chromium, rhenium, or nickel catalyst, but high-temperature and high-pressure reaction conditions such as a hydrogen pressure of 200 atm and a reaction temperature of 200° C. or higher are required.

Recently, in NPL 1 or 2, hydrogenation of an amide under low-temperature and low-pressure conditions of 120° C. and 10 atm or 160° C. and 5 atm by adding molecular sieves into a reaction system has been reported. However, there was a problem that the substrate applicability is poor, and an alcohol is produced as a by-product by C—N cleavage. In addition, such a catalyst cannot be reused.

Further, there is also a reaction using a homogeneous catalyst reported in NPL 3, however, there was a problem that an alcohol is produced as a by-product by C—N cleavage. In addition, in the reaction using a homogeneous catalyst, it is difficult to repeatedly use the expensive catalyst.

Therefore, for industrial use, a catalyst, which can be used even under mild conditions and has durability so as to enable repeated use while maintaining high activity is demanded.

CITATION LIST

Non Patent Literature

NPL 1: R. Burch, C. Paun, X. -M. Cao, P. Crawford, P. Goodrich, C. Hardacre, P. Hu, L. McLaughlin, J. Sa, J. M. Thompson, Catalytic hydrogenation of tertiary amides at low temperatures and pressures using bimetallic Pt/Re-based catalysts. J. Catal. 283, 89-97 (2011)

NPL 2: M. Stein, B. Breit, Catalytic hydrogenation of amides to amines under mild conditions. Angew. Chem. Int. Ed. 125, 2287-2290 (2013)

NPL 3: E. Balaraman, B. Gnanaprakasam, L. J. W. Shimon, D. Milstein, Direct hydrogenation of amides to alcohols and amines under mild conditions. J. Am. Chem. Soc. 132, 16756-16758 (2010)

SUMMARY OF INVENTION

Technical Problem

Accordingly, an object of the present invention is to provide a catalyst, which is a catalyst capable of carrying out a reduction reaction for converting an amide compound into an amine compound, can be used even under mild conditions, and also has durability so as to enable repeated use while maintaining high activity.

Solution to Problem

The present inventors conducted intensive studies to achieve the above-mentioned object, and as a result, they found that a catalyst which contains platinum and vanadium, and is supported on a carrier has high hydrogenation activity, selectivity, durability, and reactivity for an amide compound, and thus completed the present invention.

That is, the present invention is directed to an amide compound hydrogenation reaction catalyst characterized in that platinum and vanadium are supported on a carrier, and a method for producing the amide compound hydrogenation reaction catalyst, characterized by mixing a mixed liquid of a platinum compound and a vanadium compound with a carrier, followed by drying.

Further, the present invention is directed to a method for producing an amine compound, characterized by bringing an amide compound into contact with the above-mentioned amide compound hydrogenation reaction catalyst so as to hydrogenate the amide compound, thereby obtaining an amine compound.

Still further, the present invention is directed to an amine compound produced by the above-mentioned method for producing an amine compound.

Advantageous Effects of Invention

The catalyst of the present invention can be used under mild conditions, and therefore, synthesis of an amine compound from an amide compound becomes safe and easy.

Further, the catalyst of the present invention does not essentially require a special operation when it is produced, and therefore can be produced inexpensively and safely.

Therefore, the catalyst of the present invention can be used in industrial synthesis of an amine compound from an amide compound.

In addition, since the catalyst of the present invention is supported on a carrier, expensive platinum can be easily recovered by filtration after it is used, and further, the recovered catalyst can maintain the original activity and selectivity.

Therefore, reuse of the catalyst of the present invention is also easy.

DESCRIPTION OF EMBODIMENTS

Figure 1:
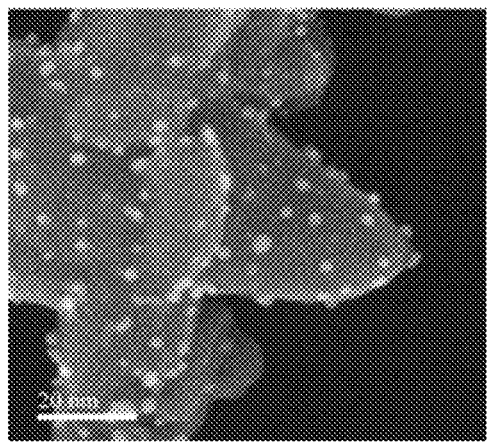
FIG. 1 is a TEM image of Pt—V/HAP that is a catalyst of the present invention.

The amide compound hydrogenation reaction catalyst of the present invention (hereinafter referred to as "the catalyst of the present invention") is a catalyst obtained by supporting platinum and vanadium on a carrier. Incidentally, in the present description, the catalyst of the present invention is sometimes denoted by "X-Y/Z" (X and Y represent a metal name such as platinum or vanadium, and Z represents a carrier name) or the like.

(Platinum)

Platinum constituting the catalyst of the present invention is not particularly limited, but is preferably, for example, platinum particles. Here, the platinum particles refer to particles of platinum selected from at least one type of metallic platinum or platinum oxide, and are preferably particles of metallic platinum.

Here, the platinum particles are not particularly limited as long as the particles contain platinum, and may contain a small amount of a noble metal such as ruthenium (Ru), rhodium (Rh), or palladium (Pd), but are preferably metallic platinum. The platinum particles may be primary particles or secondary particles. The average particle diameter of the platinum particles is preferably from 1 to 30 nm, more preferably from 1 to 10 nm. Incidentally, the "average particle diameter" as used herein refers to an average of diameters of an arbitrary number of particles observed with an electron microscope.

(Vanadium)

Vanadium constituting the catalyst of the present invention is not particularly limited, but is preferably, for example, vanadium oxide. Vanadium oxide is, for example, selected from at least one type of vanadate ions ($VO_4^{3-}$ or $VO_3^{3-}$), vanadium pentoxide, vanadium(II) oxide, vanadium (IV) oxide, etc., and is preferably $V_2O_5$.

(Molar Ratio of Platinum-Vanadium [Pt—V])

As for the compositional ratio of platinum and vanadium in the catalyst of the present invention, the molar ratio [Pt:V] is 1:0.1 to 10, preferably 1:0.5 to 5, more preferably 1:0.8 to 1.2 in terms of the number of moles of platinum (Pt) as metal:vanadium (V) as metal.

(Ruthenium)

In the catalyst of the present invention, ruthenium can be further incorporated. The ruthenium is not particularly limited, but is, for example, ruthenium oxide, metallic ruthenium, or the like. Further, metallic ruthenium may be alloyed with platinum, and ruthenium oxide may forma composite oxide with vanadium oxide. Incidentally, the alloying or the formation of a composite oxide can be carried out according to a conventional method.

When ruthenium is incorporated in the catalyst of the present invention, the above-mentioned platinum or vanadium may be partially substituted with ruthenium.

(Molar Ratio of Platinum-Ruthenium-Vanadium [Pt—Ru—V])

As for the compositional ratio of platinum, ruthenium, and vanadium in the catalyst of the present invention, the compositional ratio of platinum and vanadium is described above, and the molar ratio [Pt:Ru] is 1:0.1 to 10, preferably 1:0.5 to 5, more preferably 1:0.8 to 1.2 in terms of the number of moles of platinum (Pt) as metal:ruthenium (Ru) as metal.

(Carrier)

The carrier (base material) of the catalyst of the present invention is not particularly limited. Various physical properties such as an adsorption ability of the carrier are also not particularly limited, but for example, the adsorption ability expressed as a so-called BET value may be from 0.1 to 300 $m^2/g$, and the average particle diameter may be from 0.02 to 100 μm. In the present invention, the adsorption ability of the carrier is preferably from 0.5 to 180 $m^2/g$.

Further, the form of the carrier is not particularly limited, and examples thereof include a powder form, a spherical particulate form, an amorphous granular form, a columnar pellet form, an extruded form, and a ring form.

As the carrier as described above, for example, an inorganic oxide such as hydroxyapatite (HAP), titania, alumina, or silica, a carbon powder, or the like can be used, and it is preferably hydroxyapatite.

The hydroxyapatite is not particularly limited and includes not only calcium hydroxide phosphate having a general stoichiometric composition of $Ca_{10}(PO_4)_6(OH)_2$, but also a calcium hydroxide phosphate compound having a composition similar thereto, tricalcium phosphate, etc.

In the catalyst of the present invention, an embodiment in which platinum and vanadium are supported on the carrier is not particularly limited, and various embodiments can be adopted according to the form of the carrier, and a position where platinum and vanadium are supported may also not be simply controlled, and may be inside a pore or a layer, or only on the surface, however, it is preferred that platinum having a small particle diameter is dispersed and supported, and vanadium is present in the vicinity of platinum or on platinum. Incidentally, the supported amount of platinum and vanadium oxide on the carrier in the catalyst of the present invention is not particularly limited, but, for example, the amount of platinum in terms of metal is preferably from 0.1 to 10 wt %.

In the catalyst of the present invention, the carrier as described above is used, and therefore, separation after it is used in the reaction also becomes easy, and thus, it goes without saying that the catalyst is advantageous also for reuse of the catalyst.

(Component that can be Added to Catalyst)

The catalyst of the present invention may be any as long as the above-mentioned platinum and vanadium (ruthenium as needed) are supported on the carrier, and another catalyst, another carrier, or the like may be incorporated according to a conventional method within a range not impairing the effect.

(Method for Producing Catalyst of Present Invention)

The catalyst of the present invention can be produced by a method in which a mixed liquid of a platinum compound and a vanadium compound (a ruthenium compound as needed) is mixed with a carrier, followed by drying (hereinafter referred to as "the method of the present invention").

The platinum compound used in the method of the present invention is not particularly limited, but is preferably a compound that becomes platinum particles on the carrier when it is dried. Examples of such a platinum compound include platinum complex salts such as platinum acetylacetonate (Pt(acac)$_2$), tetraamineplatinum(II) acetate, diamminedinitro platinum(II), hexammineplatinum(IV) carbonate, bis(dibenzalacetone)platinum (0), and salts such as platinum chloride, platinum nitrate, and potassium tetrachloroplatinate, and particularly, Pt(acac)$_2$ is preferred.

Further, the vanadium compound used in the method of the present invention is not particularly limited, but is preferably a compound that forms vanadium oxide on the carrier when it is dried. Examples of such a vanadium compound include vanadium complex salts such as vanadyl acetyl acetonate (VO (acac)$_2$) and tetramethylammonium bis(tartrato)bis[oxovanadate(IV)], and salts such as ammonium vanadate(V) and vanadium naphthenate, and particularly, VO(acac)$_2$ is preferred.

Further, the ruthenium compound used in the method of the present invention is not particularly limited, and examples thereof include salts such as ruthenium chloride and ruthenium acetate, complex salts such as ruthenium acetylacetonate, triruthenium(0) dodecacarbonyl, ruthenium (I) formatodicarbonyl, ruthenium(II) nitrosyl nitrate, and hexammineruthenium acetate. Among these, ruthenium chloride and Ru(acac)$_3$ are preferred.

The mixed liquid used in the method of the present invention is a liquid obtained by suspending the platinum compound and the vanadium compound (the ruthenium compound as needed) in a solvent. Examples of the solvent include water and organic solvents such as an alcohol and acetone, and one type or two or more types of these solvents may be combined. In the mixed liquid, the molar ratio of the platinum compound and the vanadium compound is 1:0.1 to 10, preferably 1:0.5 to 5, more preferably 1:1. When the ruthenium compound is incorporated therein, the above-mentioned platinum compound or vanadium compound may be partially substituted with the ruthenium compound. Incidentally, the temperature of the solvent is not particularly limited, but is, for example, from 0 to 100° C., preferably from 10 to 50° C.

The thus prepared mixed liquid is subsequently mixed with the carrier. The method for mixing the mixed liquid with the carrier is not particularly limited and may be any as long as the amount of thereof allows the respective components to be sufficiently dispersed therein, and mixing is performed while stirring such that the amount of the carrier is from 0.1 to 100 g, preferably from 1 to 10 g with respect to 0.1 mmol of platinum in terms of metal. After mixing, stirring is continued for 0.5 to 12 hours, preferably for 1 to 3 hours.

After the mixed liquid and the carrier are mixed as described above, the resulting material may be dried. Before drying, it is preferred to remove the solvent by performing a pretreatment such as washing, filtration, concentration, or the like. The drying conditions are not particularly limited, but for example, drying is performed at 80 to 200° C. for 1 to 56 hours. After drying, it is preferred to perform firing or the like at 250 to 700° C. for 1 to 12 hours using, for example, a muffle furnace or the like, and grinding or the like may be further performed.

In the thus obtained catalyst of the present invention, platinum and vanadium (ruthenium as needed) are supported on the carrier.

Incidentally, whether the catalyst of the present invention can be produced can be confirmed using, for example, a TEM (Transmission Electron Microscope), an FE-SEM (Field Emission-Scanning Electron Microscope), EDX (Energy Dispersive X-ray Spectroscopy), or the like.

(Hydrogenation of Amide Compound)

The catalyst of the present invention is for use in a hydrogenation reaction of an amide compound. Therefore, by bringing the catalyst of the present invention into contact with an amide compound, the amide compound is hydrogenated (reduced), whereby an amine compound can be produced.

The amide compound is not particularly limited as long as it is a compound having an amide bond, but is preferably, for example, a secondary or higher amide compound or an amide compound containing an aromatic substituent, an amide compound in which two substituents, which are bonded to the N atom in a lactam or a tertiary amide and do not contain carbonyl, are linked to each other so as to have a cyclic structure, or the like, and a secondary or higher amide compound or an amide compound containing an aromatic substituent is more preferred.

The method for bringing the catalyst of the present invention into contact with an amide compound so as to hydrogenate the amide compound is not particularly limited and may be appropriately selected. Specifically, hydrogenation of an amide compound may be performed by bringing the catalyst of the present invention, the amide compound, and hydrogen gas into contact with one another in a liquid phase in a pressure-resistant vessel such as an autoclave. Further, in the hydrogenation, in order for the reaction to proceed by removing water, molecular sieves or the like may be placed in the vessel in advance. Further, the catalyst of the present invention may be subjected to a reducing treatment in advance prior to the hydrogenation.

The liquid phase is preferably only an organic solvent or a mixed liquid of several types of organic solvents, and more preferably only an organic solvent. The organic solvent used above is not particularly limited, and for example, one or more types selected from aliphatic hydrocarbons having 5 to 20 carbon atoms such as dodecane and cyclohexane, aromatic hydrocarbons having 7 to 9 carbon atoms such as toluene and xylene, ethers having a chain structure or a cyclic structure such as dimethyl ether, dimethoxyethane (DME), oxetane, tetrahydrofuran (THF), tetrahydropyran (THP), dibenzofuran, and furan, polyethers such as polyethylene glycol and polypropylene glycol, and the like are exemplified, and among these, DME is particularly preferred.

The used amount of the organic solvent is preferably, for example, within a range so that the concentration of the amide compound is from about 0.5 to 2.0 mass %. Further, the used amount of the catalyst of the present invention is, for example, based on the amount of platinum in the catalyst, from about 0.0001 to 50 mol %, preferably from about 0.01 to 20 mol %, more preferably from about 0.1 to 5 mol with respect to the amide compound.

The catalyst of the present invention can allow a hydrogenation reaction to proceed smoothly even under mild conditions. The reaction temperature can be appropriately adjusted according to the type of a substrate, the type of a target product, or the like, and is, for example, 100° C. or lower, preferably from 10 to 100° C., more preferably from about 20 to 80° C., particularly preferably from about 30 to 70° C. The pressure during the reaction is 5 MPa or less, preferably from normal pressure to 4 MPa, more preferably from 2 to 3.5 MPa. The reaction time can be appropriately adjusted according to the reaction temperature and pressure, and is, for example, from about 10 minutes to 56 hours, preferably from about 20 minutes to 48 hours, particularly preferably from about 40 minutes to 30 hours.

An amine compound is obtained by hydrogenating an amide compound by the above-mentioned method, however, even an amine compound that is difficult to produce by an ordinary cross-coupling reaction or the like can be produced by the method of the present invention. Specifically, in a Buchwald-Hartwig reaction that is a representative example of C—N coupling, halogenated aryl and a primary or secondary amine are reacted with each other in the presence of a Pd catalyst, whereby an aryl group can be directly bound to the N atom of the amine, but one or more carbon atoms or methylene chains cannot be interposed between the N atom and an aromatic ring. However, in the above-mentioned method, an amide compound obtained by acylating the N atom of an amine is hydrogenated, and as a result, a C—N bond in which one or more carbon atoms or methylene chains are interposed can be formed for the N atom of the original amine. As such an example, morpholine→4-cyclohexylcarbonyl morpholine→4-cyclohexylmethyl morpholine, piperidine→1-phenylacetylpiperidine→1-phenethylpiperidine, benzylmethylamine→benzylmethylphenylacetylamidebenzylmethylphenethylamine, etc. are exemplified.

(Reuse of Catalyst)

In the catalyst of the present invention, platinum that is an active component is supported on the carrier, and therefore, the supported platinum is hardly transformed into large particles even during the reaction. Further, the catalyst of the present invention can be easily recovered from the reaction solution after hydrogenation by a physical separation method such as filtration or centrifugation. The recovered catalyst of the present invention can be reused as it is or after being subjected to washing, drying, firing, or the like as needed. The washing, drying, firing, or the like may be performed in the same manner as in the production of the catalyst of the present invention.

The recovered catalyst of the present invention can exhibit substantially the same catalytic activity as the unused catalyst of the present invention, and even if use and regeneration are repeated a plurality of times, a decrease in the catalytic activity can be remarkably suppressed. Therefore, according to the present invention, the catalyst that generally accounts for a large proportion of the cost of hydrogenation can be recovered and used repeatedly, so that the cost of hydrogenation of an amide compound can be largely reduced.

EXAMPLES

Hereinafter, the catalyst of the present invention and Examples of the present invention will be specifically described, however, the present invention is not limited to the following Examples, and can be widely applied within the scope of the gist of the present invention.

Production Example 1

Preparation of Pt—V/HAP:

To 90 mL of acetone, 0.4 mmol of $Pt(acac)_2$ manufactured by N.E. CHEMCAT Corporation, and 0.4 mmol of $VO(acac)_2$ of Sigma-Aldrich Co. LLC were added, followed by stirring at room temperature for 30 minutes. Further, 1.0 g of HAP (trade name "tricalcium phosphate") of Wako Pure Chemical Industries, Ltd. was added thereto, followed by stirring at room temperature for 4 hours. The solvent was removed from the obtained mixture using a rotary evaporator, whereby a light green powder was obtained. The obtained powder was dried overnight at 110° C. Further, the dried powder was ground with an agate mortar and then fired in the atmosphere at 300° C. for 2 hours, whereby a dark gray powder (Pt—V/HAP) was obtained.

Figure 2:
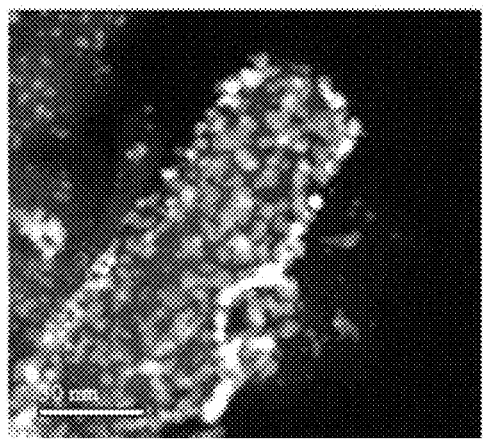
FIG. 2 is an ADF-STEM image of Pt—V/HAP obtained in Production Example 1.
Figure 3:
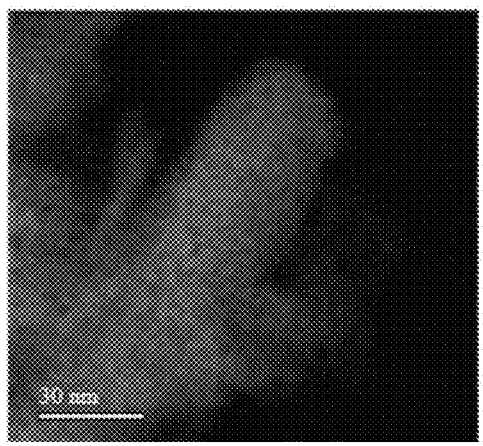
FIG. 3 is an elemental mapping image of Ca of Pt—V/HAP obtained in Production Example 1.
Figure 4:
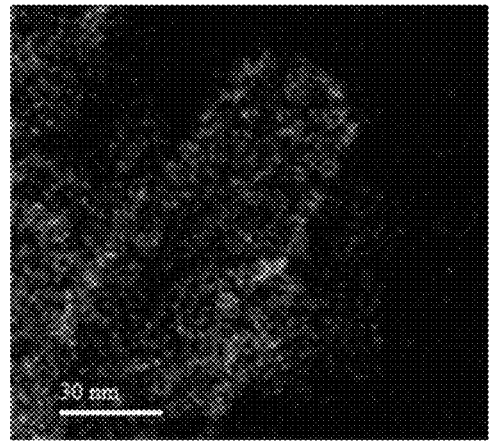
FIG. 4 is an elemental mapping image of V of Pt—V/HAP obtained in Production Example 1.
Figure 5:
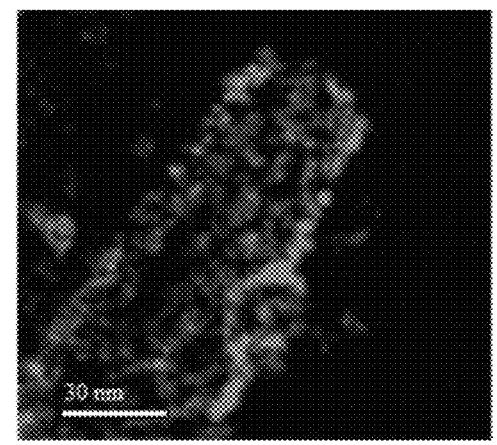
FIG. 5 is an elemental mapping image of Pt of Pt—V/HAP obtained in Production Example 1.
Figure 6:
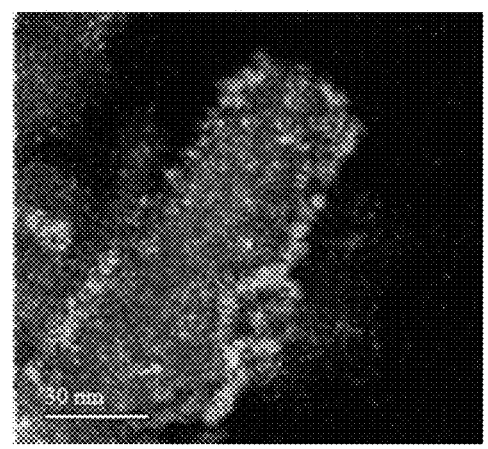
FIG. 6 is an image obtained by overlapping the elemental mapping images of Ca, V, and Pt of Pt—V/HAP obtained in Production Example 1.
Figure 7:
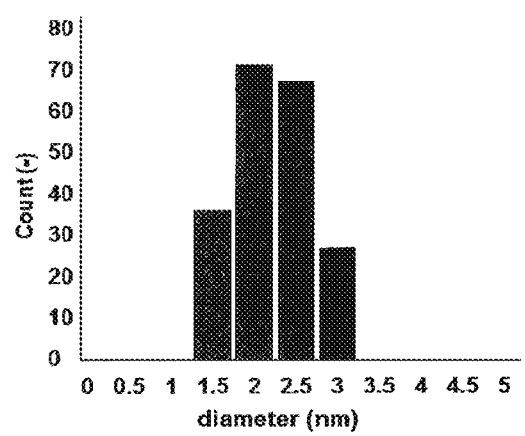
FIG. 7 is a view showing results of an EDS line analysis of Pt—V/HAP obtained in Production Example 1.

For Pt—V/HAP obtained above, various analyses were performed. A TEM image of Pt—V/HAP is shown in FIG. 1, an ADF STEM image is shown in FIG. 2, an elemental mapping image of Ca is shown in FIG. 3, an elemental mapping image of V is shown in FIG. 4, an elemental mapping image of Pt is shown in FIG. 5, and an image obtained by overlapping the elemental mapping images of Ca, V, and Pt is shown in FIG. 6. From these results, it was found that in the catalyst of the present invention, platinum particles are supported on the carrier, vanadium oxide ($V_2O_5$) is present in the vicinity or on the platinum particles, the molar ratio [Pt:V] is 6:7 in terms of the number of moles of platinum (Pt) as metal:vanadium (V) as metal, and the amount of platinum as metal is 5.8 wt %. Further, from the result of an EDS line analysis of Pt—V/HAP, the average particle diameter of the platinum particles was 2.2 nm.

Production Example 2

Preparation of Pt—V/C:

Pt—V/C was obtained in the same manner except that HAP in Production Example 1 was changed to porous carbon (trade name: Carbon Mesoporous) of Sigma-Aldrich Co. LLC. It was found that the molar ratio [Pt:V] is 6:7 in terms of the number of moles of platinum (Pt) as metal: vanadium (V) as metal, and the amount of platinum as metal is 5.8 wt %.

Production Example 3

Preparation of Pt—V/$TiO_2$:

Pt—V/$TiO_2$ was obtained in the same manner except that HAP in Production Example 1 was changed to titania (JRC-TIO-4) that is a reference catalyst of the Catalyst Society of Japan. It was found that the molar ratio [Pt:V] is 6:7 in terms of the number of moles of platinum (Pt) as metal:vanadium (V) as metal, and the amount of platinum as metal is 5.8 wt %.

Production Example 4

Preparation of Pt—V/$Al_2O_3$:

Pt—V/$Al_2O_3$ was obtained in the same manner except that HAP in Production Example 1 was changed to alumina (AKP-G015) of Sumitomo Chemical Company, Limited. It was found that the molar ratio [Pt:V] is 6:7 in terms of the number of moles of platinum (Pt) as metal:vanadium (V) as metal, and the amount of platinum as metal is 5.8 wt %.

Production Example 5

Preparation of Pt—V/$SiO_2$:

Pt—V/$SiO_2$ was obtained in the same manner except that HAP in Production Example 1 was changed to silica (Q-3) of Fuji Silysia Chemical, Ltd. It was found that the molar ratio [Pt:V] is 6:7 in terms of the number of moles of platinum (Pt) as metal:vanadium (V) as metal, and the amount of platinum as metal is 5.8 wt %.

Production Example 6

Preparation of Pt—Ru—V/$TiO_2$:

To 90 mL of water, 5.0 mL of a 40 mM aqueous solution of $RuCl_3$ (Ru: 0.2 mmol) manufactured by N. E. CHEMCAT Corporation, 0.5 g of $TiO_2$, and 0.085 g of $K_2(PtCl_4)$ (Pt: 0.2 mmol) were added, and further 5.0 mL of a 40 mM aqueous solution of VCl₃ (V: 0.2 mmol) was added thereto, followed by stirring at room temperature for 6 hours. To the obtained mixture, 1.0 mL of a 28 wt % ammonia solution was added, followed by heating and stirring at 90° C. for 6 hours. The solution was subjected to filtration and washing with deionized water, and the obtainer powder was dried overnight at 110° C. The dried powder was ground with an agate mortar, whereby a gray powder (Pt—Ru—V/HAP) was obtained. As for the ratio of metals in the obtained powder, the molar ratio [Pt:Ru:V] was 1:1:1 in terms of the number of moles of platinum (Pt) as metal:ruthenium (Ru) as metal:vanadium (V) as metal, and the amount of platinum as metal was 7.8 wt %.

Production Example 7

Preparation of Pt—Re/HAP:
Pt—Re/HAP was obtained in the same manner except that VO(acac)₂ in Production Example 1 was changed to Re₂(CO)₄₀ of Strem Chemicals, Inc. It was found that the molar ratio [Pt:Re] is 6:7 in terms of the number of moles of platinum (Pt) as metal:rhenium (Re) as metal, and the amount of platinum as metal is 5.8 wt %.

Production Example 8

Preparation of Pt—Mo/HAP:
Pt—Mo/HAP was obtained in the same manner except that VO (acac)₂ in Production Example 1 was changed to (NH₄)₆Mo₇O₂₄·4H₂O of Nacalai Tesque, Inc. It was found that the molar ratio [Pt:Mo] is 6:7 in terms of the number of moles of platinum (Pt) as metal:molybdenum (Mo) as metal, and the amount of platinum as metal is 5.8 wt %.

Production Example 9

Preparation of Pt—W/HAP:
Pt—W/HAP was obtained in the same manner except that VO (acac)₂ in Production Example 1 was changed to (NH₄)₁₀H₂(W₂O₇)₆·xH₂O of Sigma-Aldrich Co. LLC. It was found that the molar ratio [Pt:W] is 6:7 in terms of the number of moles of platinum (Pt) as metal:tungsten (W) as metal, and the amount of platinum as metal is 5.8 wt %.

Production Example 10

Preparation of Pd—V/HAP:
Pd—V/HAP was obtained in the same manner except that Pt(acac)₂ manufactured by N.E. CHEMCAT Corporation in Production Example 1 was changed to Pd(acac)₂ of Sigma-Aldrich Co. LLC. It was found that the molar ratio [Pd:V] is 6:7 in terms of the number of moles of palladium (Pd) as metal:vanadium (V) as metal, and the amount of palladium as metal is 3.2 wt %.

Production Example 11

Preparation of Ru—V/HAP:
Ru—V/HAP was obtained in the same manner except that Pt(acac)₂ manufactured by N.E. CHEMCAT Corporation in Production Example 1 was changed to Ru(acac)₃ manufactured by N.E. CHEMCAT Corporation. It was found that the molar ratio [Ru:V] is 6:7 in terms of the number of moles of ruthenium (Ru) as metal:vanadium (V) as metal, and the amount of ruthenium as metal is 3.0 wt %.

Production Example 12

Preparation of Rh—V/HAP:
Rh—V/HAP was obtained in the same manner except that Pt(acac)₂ manufactured by N.E. CHEMCAT Corporation in Production Example 1 was changed to Rh(acac)₃ of Mitsuwa Chemical Co., Ltd. It was found that the molar ratio [Rh:V] is 6:7 in terms of the number of moles of rhodium (Rh) as metal:vanadium (V) as metal, and the amount of rhodium as metal is 3.1 wt %.

Production Example 13

Preparation of Pt/HAP:
Pt/HAP was obtained in the same manner except that VO(acac)₂ in Production Example 1 was excluded. It was found that the amount of platinum as metal is 5.8 wt %.

Production Example 14

Preparation of V/HAP:
V/HAP was obtained in the same manner except that Pt(acac)₂ manufactured by N.E. CHEMCAT Corporation in Production Example 1 was excluded. It was found that the amount of vanadium as metal is 1.8 wt %.

Example 1

Each of the catalysts obtained in Production Examples 1 to 14 in a catalytic amount shown in Table 1, 5 mL of 1,2-dimethoxyethane (DME) that is a solvent, and 0.5 mmol of N-acethylmorpholine that is a substrate were added to a 50 mL autoclave made of stainless steel, and a hydrogenation reaction was carried out under the conditions shown in Table 1. After the reaction, the yield of 2 was measured using a gas chromatograph. The results are shown in Table 1.

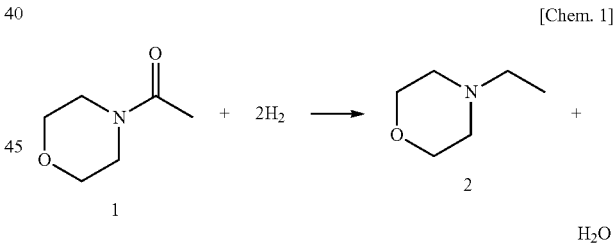

[Chem. 1]

TABLE 1

| Catalyst | Catalytic amount (g) | Reaction temperature (° C.) | Hydrogen pressure (MPa) | Reaction time (h) | Yield (%) |
|---|---|---|---|---|---|
| Pt—V/HAP | 0.1 | 70 | 3 | 1 | 70 |
| | 0.1 | 70 | 3 | 8 | 99 |
| | 0.3 | 25 | 3 | 24 | 93 |
| | 0.3 | 25 | 0.5 | 48 | 85 |
| | 0.3 | 70 | 0.1 | 48 | 95 |
| Pt—V/C | 0.1 | 70 | 3 | 1 | 47 |
| Pt—V/TiO₂ | 0.1 | 70 | 3 | 1 | 41 |
| Pt—V/Al₂O₃ | 0.1 | 70 | 3 | 1 | 59 |
| Pt—V/SiO₂ | 0.1 | 70 | 3 | 1 | 35 |
| Pt—Ru—V/TiO₂ | 0.1 | 70 | 3 | 1 | 40 |
| Pt—Ru—V/TiO₂* | 0.1 | 70 | 3 | 1 | 99 |

TABLE 1-continued

| Catalyst | Catalytic amount (g) | Reaction temperature (° C.) | Hydrogen pressure (MPa) | Reaction time (h) | Yield (%) |
|---|---|---|---|---|---|
| Pt—Re/HAP | 0.1 | 70 | 3 | 1 | 0 |
| Pt—Mo/HAP | 0.1 | 70 | 3 | 1 | 3 |
| Pt—W/HAP | 0.1 | 70 | 3 | 1 | 4 |
| Pd—V/HAP | 0.1 | 70 | 3 | 1 | 5 |
| Ru—V/HAP | 0.1 | 70 | 3 | 1 | 0 |
| Rh—V/HAP | 0.1 | 70 | 3 | 1 | 6 |
| Pt/HAP | 0.1 | 70 | 3 | 1 | 0 |
| V/HAP | 0.1 | 70 | 3 | 1 | 0 |

*pretreatment with $H_2$ at 20 (atm) and 160° C.

It was found that the catalyst in which at least both platinum and vanadium were supported can carry out the hydrogenation reaction of the amide compound under mild conditions. Further, it was found that Pt—V/HAP can carryout the hydrogenation reaction of the amide compound with good yield under mild conditions. In addition, it was found that Pt—Ru—V/TiO$_2$ also allows the reaction to proceed without any problems.

Example 2

Pt—V/HAP obtained in Production Example 1 in a catalytic amount shown in Table 2, 0.5 mmol of a substrate shown in Table 2, and 0.1 g of molecular sieves 4 Å of Wako Pure Chemical Industries, Ltd. were added to a 50 mL autoclave made of stainless steel, and 5 mL of 1,2-dimethoxyethane (DME) that is a solvent was added thereto, and then, a hydrogenation reaction was carried out at a reaction temperature of 70° C. and a hydrogen pressure of 3 MPa. After the reaction, the yield of 4 was measured using a gas chromatograph. The results are shown in Table 2.

[Chem. 2]

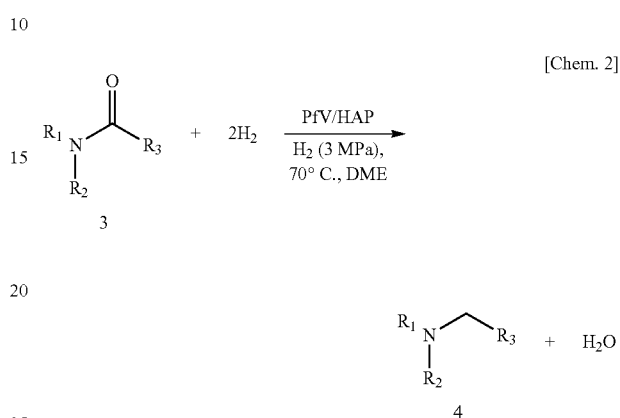

TABLE 2

| Substrate | Product | Catalytic amount (g) | Reaction time (h) | Conversion ratio (%) | Yield of 4 (%) |
|---|---|---|---|---|---|
| 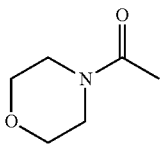 | 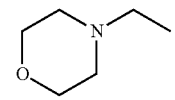 | 0.1 | 8 | >99 | 99 |
| 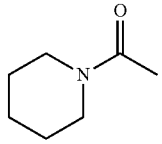 | 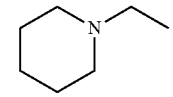 | 0.3 | 18 | 99 | 97 |
| 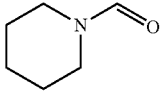 | 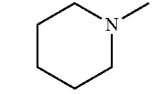 | 0.3 | 36 | 92 | 88 |
| 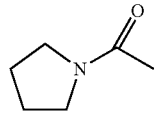 | 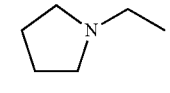 | 0.3 | 18 | 96 | 91 |
| 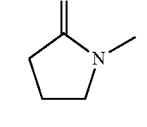 | 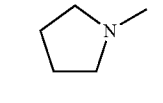 | 0.3 | 48 | 92 | 88 |
| 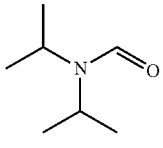 | 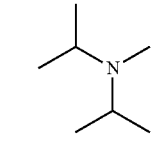 | 0.3 | 18 | 99 | 99 |

TABLE 2-continued

| Substrate | Product | Catalytic amount (g) | Reaction time (h) | Conversion ratio (%) | Yield of 4 (%) |
|---|---|---|---|---|---|
| N,N-dibutylformamide | N,N-dibutylmethylamine | 0.3 | 36 | 86 | 82 |
| N,N-dimethyloctanamide | N,N-dimethyloctylamine | 0.3 | 18 | 94 | 90 |
| morpholine cyclohexanecarboxamide | 4-(cyclohexylmethyl)morpholine | 0.1 | 48 | 97 | 96 |
| piperidine cyclohexanecarboxamide | 1-(cyclohexylmethyl)piperidine | 0.1 | 48 | 85 | 85 |
| N-butylpropanamide | N-butylpropylamine | 0.3 | 24 | 90 | 88 |
| N-tert-butylacetamide | N-tert-butylethylamine | 0.3 | 24 | 81 | 80 |
| caprolactam | azepane | 0.3 | 24 | 92 | 90 |
| acetanilide | N-ethylaniline | 0.1 | 6 | 65 | 22 |
| 4'-fluoroacetanilide | N-ethyl-4-fluoroaniline | 0.1 | 4 | 78 | 50 |
| 4-(phenylacetyl)morpholine | 4-phenethylmorpholine | 0.1 | 8 | 99 | 96 |
| 1-(phenylacetyl)piperidine | 1-phenethylpiperidine | 0.1 | 24 | 90 | 88 |

TABLE 2-continued

| Substrate | Product | Catalytic amount (g) | Reaction time (h) | Conversion ratio (%) | Yield of 4 (%) |
|---|---|---|---|---|---|
| 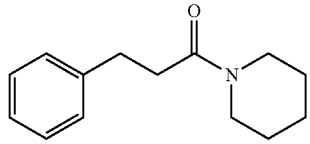 [SMILES: O=C(CCc1ccccc1)N1CCCCC1] | 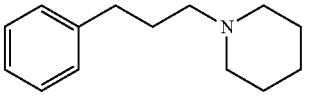 [SMILES: c1ccc(CCCN2CCCCC2)cc1] | 0.2 | 24 | 97 | 93 |
| 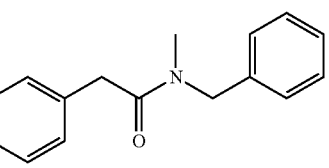 | 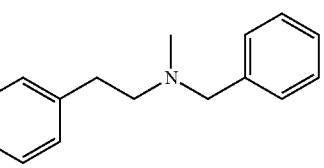 | 0.3 | 48 | 83 | 76 |
| 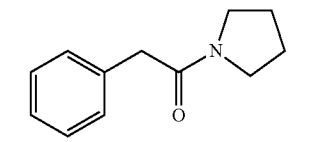 [SMILES: O=C(Cc1ccccc1)N1CCCC1] | 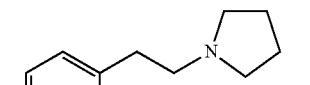 | 0.3 | 48 | 92 | 88 |
| 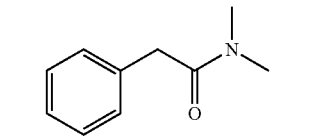 | 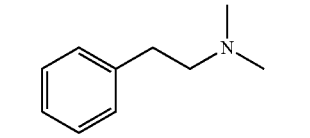 | 0.1 | 24 | 98 | 93 |

It was found that Pt—V/HAP can carry out the hydrogenation reaction of the amide compound with good yield under mild conditions even if the substrate is changed.

Example 3

Reuse of Catalyst:

After the reaction in Example 1, the used Pt—V/HAP was separated by centrifugation, washed with 1,2-dimethoxyethane (DME) that is the solvent, and then, recovered from the reaction system. The recovered Pt—V/HAP was used again in the same reaction. The results are shown in Table 3.

TABLE 3

| Catalyst | Usage count of catalyst (count) | Reaction time (h) | Conversion ratio (%) | Yield (%) |
|---|---|---|---|---|
| Pt—V/HAP | 1 | 8 | >99 | 99 |
| | 2 | 8 | 99 | 99 |
| | 3 | 8 | 99 | 99 |
| | 4 | 8 | 98 | 98 |
| | 5 | 8 | 99 | 99 |
| | 6 | 8 | 99 | 99 |
| | 7 | 8 | 98 | 98 |
| | 8 | 8 | 99 | 99 |
| | 9 | 8 | 97 | 97 |
| | 10 | 8 | 99 | 99 |

It was found that Pt—V/HAP can be reused without deterioration of the performance.

INDUSTRIAL APPLICABILITY

The catalyst of the present invention is useful for safely producing an amino compound that is useful in various pharmaceutical, agrochemical, and other various industrial fields under mild conditions. Further, the catalyst of the present invention can be produced inexpensively and safely.

The invention claimed is:

1. An amide compound hydrogenation reaction catalyst, comprising platinum and vanadium which are supported on a carrier, wherein the carrier is hydroxyapatite.

2. The amide compound hydrogenation reaction catalyst of claim 1, wherein the amide compound is a secondary or higher amide compound or an amide compound comprising an aromatic substituent.

3. The amide compound hydrogenation reaction catalyst of claim 1, further comprising ruthenium which is supported on the carrier.

4. A method for producing an amine compound, the method comprising contacting an amide compound with the amide compound hydrogenation reaction catalyst of claim 1, to hydrogenate the amide compound, thereby obtaining an amine compound.

5. The method of claim 4, wherein the hydrogenation is carried out at 100° C. or lower.

6. The method of claim 4, wherein the hydrogenation is carried out at 5 MPa or less.

7. The method of claim 4, wherein the amide compound is a secondary or higher amide compound or an amide compound comprising an aromatic substituent.

8. A method for producing the amide compound hydrogenation reaction catalyst of claim 1, the method comprising mixing a mixed liquid of a platinum compound and a vanadium compound with the carrier which is hydroxyapatite, followed by drying.

9. The method of claim 8, wherein the mixed liquid of the platinum compound and the vanadium compound is a liquid obtained by suspending the platinum compound and the vanadium compound in a solvent.

10. The method of claim 9, wherein the solvent is water.

11. The method of claim 8, wherein the mixed liquid further comprises a ruthenium compound.

12. The amide compound hydrogenation reaction catalyst of claim 1, wherein a molar ratio of the platinum and vanadium supported on the hydroxyapatite carrier is platinum:vanadium of 1:0.8 to 5.

* * * * *